Feb. 14, 1967 N. M. DARROW ETAL Plant Pat. 2,714
MANDARIN ORANGE PLANT
Filed Oct. 18, 1965
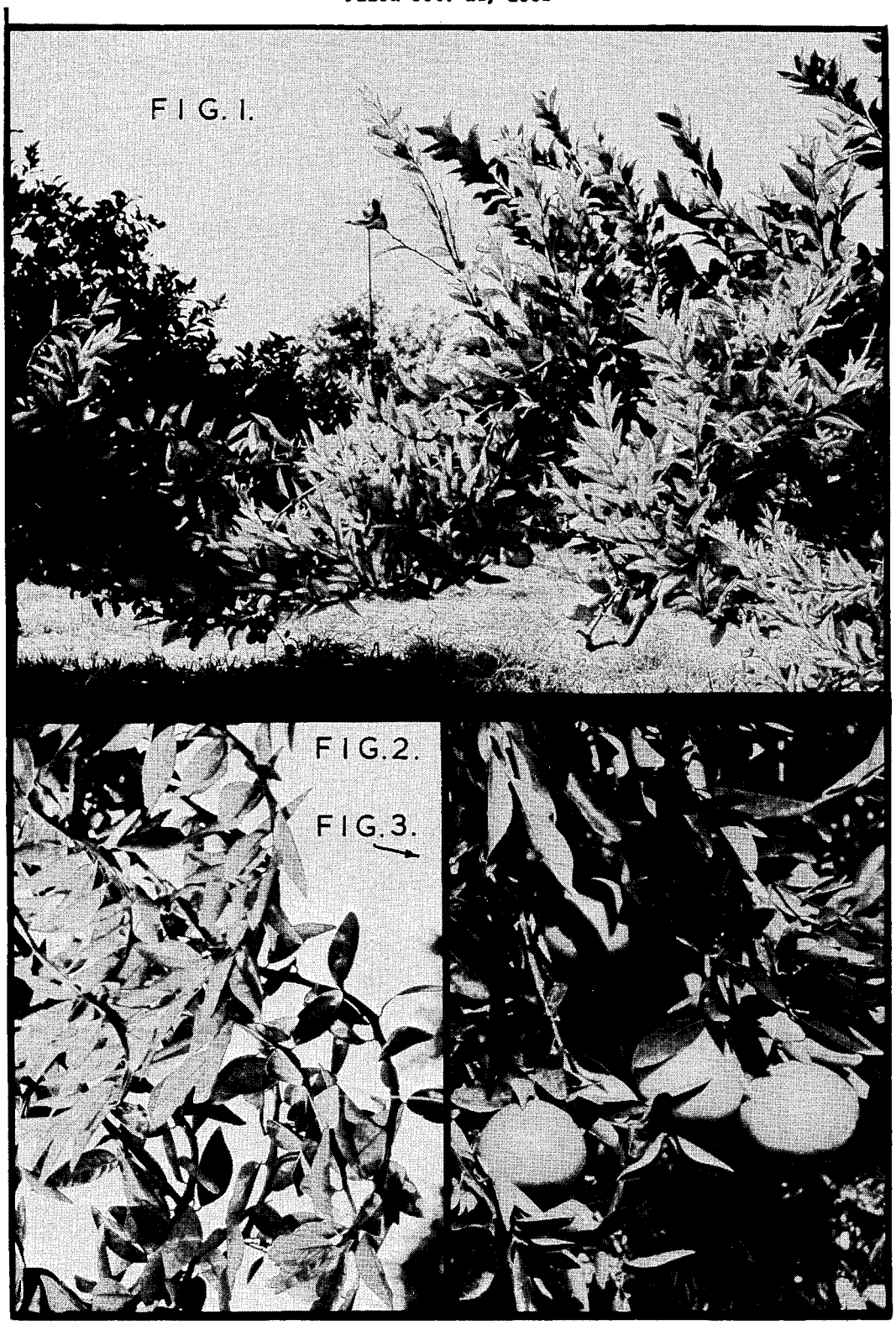
INVENTORS
Nance Marion Darrow and
Robin James Darrow
By Sparrow and Sparrow
ATTORNEYS United States Patent Office Plant Pat. 2,714
Patented Feb. 14, 1967

2,714
MANDARIN ORANGE PLANT

Nance Marion Darrow and Robin James Darrow, both of Box 81, Gayndah, Queensland, Australia Filed Oct. 18, 1965, Ser. No. 497,573
1 Claim. (Plt.—45)

This invention relates to a citrus plant derived as a mutant or sport from the variety of mandarin orange known as "Ellendale Beauty" (unpatented).

The "Ellendale Beauty" variety was first noted in the 1860's. It does not breed true from seed, giving progeny with characteristics varying between the common sweet orange (*Citrus sinensis*) and the mandarin orange (*Citrus reticulata*). It is therefore thought to be a natural hybrid of *Citrus sinensis* and *Citrus reticulata.*

The plant, the subject of this invention, was derived from a mutant branch on an "Ellendale Beauty" tree growing in Portion 12V, parish of Gayndah, county of Bowen, State of Queensland, Commonwealth of Australia. This branch was first noted by us in 1959 or 1960 and was asexually reproduced by us by budding on to other "Ellendale Beauty" trees and later on to other citrus stock.

The special characteristics of the plant, as detailed below, were discovered by us when several generations of the budded plants reached maturity.

The main characteristic distinguishing this plant from other citrus plants is this:

The leaders develop in a recumbent condition.

The budded portion grows in a single leader, unless cut, to an indefinite length in the same manner as a vine.

If the tip is cut, several leaders are established each growing to indefinite length in a similar manner.

A number of successive buddings has shown that this characteristic is a stable one, each generation producing plants of the same kind within narrow limits.

The plant produces stems, leaves and fruit similar in general to the "Ellendale Beauty" variety, with the following modifications:

(a) The fruit mature later than "Ellendale Beauty" under similar conditions, and hang on the plant longer. The fruit is a medium tight-skin mandarin, less subject to loose-skin condition than "Ellendale Beauty."

(b) The stems have longitudinal raised striations, which are helical around the stem to only a very slight extent.

(c) The plant vegetatively puts out most vigourous growth. The rate of growth is much faster than the "Ellendale Beauty," and budding is very nearly 100% viable.

In the drawings:

FIG. 1 shows photographically part of a leader, having young side-leaders thereon, growing from budded stock to the right of the figure, FIG. 2 shows a close-up of young leaders on which the longitudinal striation of the stems may be seen, and FIG. 3 shows the fruit and foliage in close-up view.

What we claim is:

The new and distinct variety of mandarin orange plant as described and illustrated, having leaders developing in a recumbent position.

No references cited.

ABRAHAM G. STONE, *Primary Examiner.*

ROBERT E. BAGWILL, *Assistant Examiner.*